(12) United States Patent
Ma et al.

(10) Patent No.: US 10,682,108 B1
(45) Date of Patent: Jun. 16, 2020

(54) METHODS, SYSTEMS, AND COMPUTER READABLE MEDIA FOR THREE-DIMENSIONAL (3D) RECONSTRUCTION OF COLONOSCOPIC SURFACES FOR DETERMINING MISSING REGIONS

(71) Applicant: The University of North Carolina at Chapel Hill, Chapel Hill, NC (US)

(72) Inventors: Ruibin Ma, Durham, NC (US); Rui Wang, Chapel Hill, NC (US); Stephen Murray Pizer, Chapel Hill, NC (US); Jan-Michael Frahm, Chapel Hill, NC (US); Julian Gary Rosenman, Chapel Hill, NC (US); Sarah Kelly McGill, Chapel Hill, NC (US)

(73) Assignee: THE UNIVERSITY OF NORTH CAROLINA AT CHAPEL HILL, Chapel Hill, NC (US)

(*) Notice: Subject to any disclaimer, the term of this patent is extended or adjusted under 35 U.S.C. 154(b) by 0 days.

(21) Appl. No.: 16/513,632

(22) Filed: Jul. 16, 2019

(51) Int. Cl.
| | |
|---|---|
| *A61B 6/00* | (2006.01) |
| *A61B 1/31* | (2006.01) |
| *G06T 15/20* | (2011.01) |
| *G06T 7/20* | (2017.01) |

(Continued)

(52) U.S. Cl.
CPC ............ *A61B 6/466* (2013.01); *A61B 1/31* (2013.01); *G06T 7/0012* (2013.01); *G06T 7/136* (2017.01); *G06T 7/20* (2013.01); *G06T 15/205* (2013.01); *G06T 2207/30032* (2013.01); *G06T 2219/2004* (2013.01)

(58) Field of Classification Search
CPC ........ G06T 7/0012; G06T 7/20; G06T 7/136; G06T 15/205; A61B 1/31; A61B 6/466
See application file for complete search history.

(56) References Cited

U.S. PATENT DOCUMENTS

| | | |
|---|---|---|
| 2007/0013710 A1 | 1/2007 | Higgins et al. |
| 2008/0058593 A1* | 3/2008 | Gu ................. G06T 7/0012 600/109 |
| 2015/0313503 A1 | 11/2015 | Seibel et al. |

(Continued)

OTHER PUBLICATIONS

Richard J. Chen et al "SLAM Endoscopy enhanced by adversarial depth prediction" Jun. 2019. (Year: 2019).*

(Continued)

*Primary Examiner* — Leon Flores
(74) *Attorney, Agent, or Firm* — Jenkins, Wilson, Taylor & Hunt, P.A.

(57) ABSTRACT

Methods, systems, and computer readable media for deriving a three-dimensional (3D) surface from colonoscopic video are disclosed. According to one method for deriving a 3D surface from colonoscopic video, the method comprises: performing video frame preprocessing to identify a plurality of keyframes of a colonoscopic video, wherein the video frame preprocessing includes informative frame selection and keyframe selection; generating, using a recurrent neural network and direct sparse odometry, camera poses and depth maps for the keyframes; and fusing, using SurfelMeshing and the camera poses, the depth maps into a three-dimensional (3D) surface of a colon portion, wherein the 3D surface indicates at least one region of the colon portion that was not visualized.

16 Claims, 10 Drawing Sheets

(51) Int. Cl.
G06T 7/136 (2017.01)
G06T 7/00 (2017.01)

(56) References Cited

U.S. PATENT DOCUMENTS

| | | | |
|---|---|---|---|
| 2015/0320514 A1 | 11/2015 | Ahn et al. | |
| 2017/0046833 A1* | 2/2017 | Lurie | G06T 19/20 |
| 2018/0253839 A1* | 9/2018 | Zur | A61B 1/00009 |
| 2018/0317740 A1 | 11/2018 | Rossetto et al. | |

OTHER PUBLICATIONS

Wang et al., "Improving 3D Surface Reconstruction from Endoscopic Video via Fusion and Refined Reflectance Modeling", pp. 1-7 (2017).
Zhao et al., "Orthotropic Thin Shell Elasticity Estimation for Surface Registration", pp. 1-12 (2017).
Ilg et al., "FlowNet 2.0: Evolution of Optical Flow Estimation with Deep Networks", pp. 2462-2470 (Dec. 6, 2016).
Ourselin et al., "Medical Image Computing and Computer-Assisted Intervention—MICCAI 2016", 19th International Conference, Springer, pp. 1-723 (Oct. 17-21, 2016).
Mayer et al., "A Large Dataset to Train Convolutional Networks for Disparity, Optical Flow, and Scene Flow Estimation", pp. 1-14 (Dec. 7, 2015).
Bartoli et al., "Shape-from-Template", IEEE Transaction on Pattern Analysis and Machine Intelligence, vol. 37, No. 10, pp. 2099-2118 (Oct. 2015).
Simonyan et al., "Very Deep Convolutional Networks for Large-Scale Image Recoginition", ICLR Conference Paper, pp. 1-14 (2015).
Zollhöfer et al., "Shading-based Refinement on Volumetric Signed Distance Functions", pp. 1-14 (2015).
Zhao et al., "Surface Registration in the Presence of Missing Patches and Topology Change", pp. 1-6 (2015).
Malti et al., "Combining Conformal Deformation and Cook-Torrance Shading for 3-D Reconstruction in Laparoscopy", IEEE Transactions on Biomedical Engineering, vol. 61, No. 6, pp. 1684-1692 (Jun. 2014).
Mair-Hein et al., "Optical techniques for 3D surface reconstruction in computer-assisted laparoscopic surgery", pp. 1-58 (2013).
Zeng et al., "A Generic Deformation Model for Dense Non-Rigid Surface Registration: a Higher-Order MRF-based Approach", pp. 3360-3367 (2013).
Tokgozoglu et al., "Color-Based Hybrid Reconstruction for Endoscopy", IEEE Computer Society Conference on Computer Vision and Pattern Recognition Workshops, pp. 8-15 (2012).
"Malti et al.," Template-Based Conformal Shape-from-Motion from Registered Laparoscopic Images, pp. 1-5 (2012).
"Malti et al.," Template-Based Conformal Shape-from-Motion-and-Shading for Laparoscopy, pp. 1-10 (2012).
Wu, et al. "Shading-based Dynamic Shape Refinement from Multi-view Video under General Illumination", Conference Paper, IEEE International Conference on Computer Vision, pp. 1-9 (Nov. 2011).
Bauer et al., "A New Riemannian Setting for Surface Registration", pp. 182-193 (2011).
Han et al., "High Quality Shape from a Single RGB-D Image under Uncalibrated Natural Illumination", pp. 1-8 (2010).
Salzmann et al., "Deformable Surface 3D Reconstruction from Monocular Images", pp. 1-104 (2010).
Zaharescu et al., "Surface Feature Detection and Description with Applications to Mesh Matching", CVPR—IEEE International Conference on Computer Vision and Pattern Recognition, pp. 1-9 (Jun. 2009).
Sun et al., "A Concise and Provably Informative Multi-Scale Signature Based on Heat Diffusion", Eurographics Symposium on Geometry Processing, vol. 28, No. 5, pp. 1-10 (2009).
Durou et al., "Numerical methods for shape-from-shading: A new survey with benchmarks", Computer Vision and Image Understanding, Elsevier, pp. 22-43 (2008).
Ahmed et al., "A New Formulation for Shape from Shading for Non-Lambertian Surfaces", IEEE Computer Society Conference on Computer Vision and Pattern Recognition (CVPR '06), pp. 1-8 (2006).
Paragios et al., "Handbook of Mathematical Models in Computer Vision", Springer, pp. 1-612 (2006).
Bronstein et al., "Generalized multidimensional scaling: A framework for isometry-invariant partial surface matching", pp. 1168-1172 (Dec. 5, 2005).
Gatzke et al., "Curvature Maps for Local Shape Comparison", pp. 1-9 (Jul. 2005).
Prados et al., "Shape from Shading: a well-posed problem?", IEEE Conference on Computer Vision and Pattern Recognition, CVPR, pp. 870-877 (Jun. 2005).
Gu et al., "Genus Zero Surface Conformal Mapping and Its Application to Brain Surface Mapping", IEEE Transactions on Medical Imaging, vol. 23, No. 8, pp. 949-958 (Aug. 2004).
Elad et al., "On Bending Invariant Signatures for Surfaces", IEEE Transactions on Pattern Analysis and Machine Intelligence, vol. 25, No. 10, pp. 1285-1295 (Oct. 2003).
Kao et al., "Lax-Friedrichs Sweeping Scheme for Static Hamilton-Jacobi Equations", pp. 1-35 (Aug. 1, 2003).
Kim et al., "Pharyngeal Pressure Analysis by the Finite Element Method During Liquid Bolus Swallow", pp. 585-589 (2000).
Zhang et al., "Shape from Shading: A Survey", IEEE Transactions on Pattern Analysis and Machine Intelligence, vol. 21, No. 8, pp. 690-706 (Aug. 1999).
Thirion, "Image matching as a diffusion process: an analogy with Maxwell's demons", Medical Image Analysis, Elsevier, pp. 243-260 (1998).
Koenderink et al., "Bidirectional Reflection Distribution Function expressed in terms of surface scattering modes", pp. 1-2 (1996).
Schwab et al., "Dynamic imaging of the upper airway during respiration in normal subjects", The American Physiological Society, pp. 1504-1514 (1993).
Cook et al., "A Reflectance Model for Computer Graphics", AMC Transactions on Graphics, vol. 1, No. 1, pp. 7-24 (Jan. 1982).
Horn, "Shape from Shading: A Method for Obtaining the Shape of a Smooth Opaque Object from One View", pp. 1-198 (Nov. 1970).
Schöps et al., "SurfelMeshing: Online Surfel-Based Mesh Reconstruction," IEEE Transactions on Pattern Analysis and Machine Intelligence, pp. 1-13 (Oct. 1, 2018).
Wang et al., Recurrent Neural Network for Learning Dense Depth and Ego-Motion from Video, University of North Carolina at Chapel Hill, pp. 1-18 (May 17, 2018).
Engel et al., "Direct Sparse Odometry," IEEE Transactions on Pattern Analysis and Machine Intelligence vol. 40 No. 3, pp. 611-625 (Mar. 2018).
Yin et al., "GeoNet: Unsupervised Learning of Dense Depth, Optical Flow and Camera Pose," CVPR paper, Computer Vision Foundation, pp. 1983-1992 (2018).
Tateno et al., "CNN-SLAM: Real-time dense monocular SLAM with learned depth prediction," CVPR paper, Computer Vision Foundation, pp. 6565-6574 (Jul. 2017).
Zhou et al., "Unsupervised Learning of Depth and Ego-Motion from Video," CVPR paper, Computer Vision Foundation, pp. 1851-1860 (2017).
Schönberger et al., "Structure-from-Motion Revisited," CVPR paper, Computer Vision Foundation, pp. 4104-4113 (2016).
Mur-Artal et al., "ORB-SLAM: A Versatile and Accurate Monocular SLAM System," IEEE Transactions on Robotics, pp. 1-18 (Sep. 18, 2015).
Hong et al., "3D Reconstruction of virtual colon structures from colonoscopy images," Computerized Medical Imaging and Graphics, pp. 22-33 (2014).
Engel et al., "LSD-SLAM: Large-scale Direct Monocular SLAM," Technical University Munich, pp. 1-16 (2014).
Jemal et al., "Global Patterns of Cancer Incidence and Mortality Rates and Trends," Cancer Epidemiology, Biomarkers & Prevention, pp. 1893-1907 (2010).

(56) References Cited

OTHER PUBLICATIONS

Hong et al., "Colonoscopy Simulation," SPIE, pp. 1-9 (2007).
Rijn et al., "Polyp Miss Rate Determined by Tandem Colonoscopy: A Systematic Review," American Journal of Gastroenterology, pp. 343-350 (2006).
Notice of Allowance and Fee(s) Due for U.S. Appl. No. 16/241,356 (dated Nov. 22, 2019).
Non-Final Office Action for U.S. Appl. No. 16/241,356 (dated Jul. 11, 2019).
Commonly-assigned, co-pending U.S. Appl. No. 16/241,356 for "Methods, Systems, and Computer Readable Media for Deriving a Three-Dimensional (3D) Textured Surface From Endoscopic Video," (Unpublished, filed Jan. 8, 2019).
Tavanapong et al., "Reconstruction of a 3D Virtual Colon Structure and Camera Motion for Screening Colonoscopy," Medical Research Archives, pp. 1-23 (2017).
Schoeffmann et al., "Keyframe Extraction Video," Multimedia Tools and Applications, pp. 1-20 (2015).
Kaufman et al., "3D Surface Reconstruction from Endoscopic Videos," Visualization in Medicine and Life Sciences pp. 1-14 (2008).
Thormaehlen et al., "Three-Dimensional Endoscopy," pp. 1-6 (2002).
Wang et al., "Endoscopy: Deriving a 3D Textured Surface from Endoscopic Video, Then Registration with CT," https://www.semanticscholar.org, pp. 1-12 (2019).
Fan et al., "Features for the Detection of Flat Polyps in Colonoscopy Video," MIUA 2018: Medical Image Understanding and Analysis, pp. 1-12 (2018).
Ma et al., "Skeleton-based Generalized Cylinder Deformation under the Relative Curvature Condition," Endographics Proceedings, DOI: 10.2312/p. 20181275, pp. 1-4 (2018).
McGill et al., "Missed Colonic Surface Area at Colonoscopy Can Be Calculated with Computerized 3D Reconstruction," Gastrointestinal Endoscopy, vol. 87, No. 6S, pp. 1-2 (2018).
Rosenman et al., "Registration of Nasopharynoscope Videos with Radiation Treatment Planning CT Scans," Cancer Therapy & Oncology International Journal, pp. 1-6 (May 2017).

\* cited by examiner

METHODS, SYSTEMS, AND COMPUTER READABLE MEDIA FOR THREE-DIMENSIONAL (3D) RECONSTRUCTION OF COLONOSCOPIC SURFACES FOR DETERMINING MISSING REGIONS

GOVERNMENT INTEREST

This invention was made with government support under Grant No. CA158925 awarded by the National Institutes of Health of the United States. The government has certain rights in the invention.

TECHNICAL FIELD

The subject matter described herein relates to three-dimensional (3D) surface modeling. More specifically, the subject matter relates to methods, systems, and computer readable media for 3D reconstruction of colon surfaces for determining missing regions.

BACKGROUND

Colonoscopy is a widely used medical technique to screen the human large intestine (i.e., colon) for cancer precursors. When visualized during a colonoscopy, polyps and adenomas can be identified and inspected and, if necessary, removed or excised. However, parts of the colon surface may not be visualized during a colonoscopy, and it can be hard for the endoscopist to realize that portions were missed and the extent thereof from the colonoscopic video. Non-visualization can occur for multiple reasons, e.g., lack of orientations of the colonoscope to the full circumference of parts of the colon, occlusion from colon structures, and/or stool inside the colon.

SUMMARY

Methods, systems, and computer readable media for deriving a three-dimensional (3D) surface from colonoscopic video are disclosed. According to one method for deriving a 3D surface from colonoscopic video, the method comprises performing video frame preprocessing to identify a plurality of keyframes of a colonoscopic video, wherein the video frame preprocessing includes informative frame selection and keyframe selection; generating, using a recurrent neural network and direct sparse odometry, camera poses and depth maps for the keyframes; and fusing, using SurfelMeshing and the camera poses, the depth maps into a three-dimensional (3D) surface of a colon portion, wherein the 3D surface indicates at least one region of the colon portion that was not visualized.

A system for 3D reconstruction of colon surfaces for determining missing regions is also disclosed. The system includes at least one processor and a colon surface generation module (CSGM) executable by the at least one processor. The CSGM is configured for performing video frame preprocessing to identify a plurality of keyframes of a colonoscopic video, wherein the video frame preprocessing includes informative frame selection and keyframe selection; generating, using a recurrent neural network and direct sparse odometry, camera poses and depth maps for the keyframes; and fusing, using SurfelMeshing and the camera poses, the depth maps into a three-dimensional (3D) surface of a colon portion, wherein the 3D surface indicates at least one region of the colon portion that was not visualized.

The subject matter described herein can be implemented in software in combination with hardware and/or firmware. For example, the subject matter described herein can be implemented in software executed by a processor. In one example implementation, the subject matter described herein may be implemented using a computer readable medium having stored thereon computer executable instructions that when executed by the processor of a computer control the computer to perform steps. Example computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As used herein, the terms "node" and "host" refer to at least one physical computing platform or device including one or more processors and memory.

As used herein, the term "module" refers to hardware, firmware, or software in combination with hardware and/or firmware for implementing features described herein.

BRIEF DESCRIPTION OF THE DRAWINGS

The subject matter described herein will now be explained with reference to the accompanying drawings of which.

DETAILED DESCRIPTION

Reference will now be made in detail to various embodiments of the subject matter described herein, examples of which may be illustrated in the accompanying drawings. Wherever possible, the same reference numbers will be used throughout the drawings to refer to the same or like parts.

The subject matter described herein relates to methods, systems, and computer readable media for three dimensional (3D) reconstruction of colon surfaces for determining missing regions. In accordance with some aspects of the subject matter described herein, an example deep-learning-driven simultaneous localization and mapping (SLAM) system may produce a camera trajectory and a dense reconstructed surface for colon chunks usable for displaying missing regions. The example dense SLAM system may utilize a recurrent neural network (RNN) to predict scale-consistent depth maps and camera poses of successive frames. In the example dense SLAM system, generated depth maps may be fused into a global surface using the optimized camera poses. Advantageously, by reconstructing dense colon surface from video, endoscopists can realize missed colon surface which can lead to better, more complete inspection of colon surface and potentially more removals of precancerous polyps.

INTRODUCTION

Figure 1:
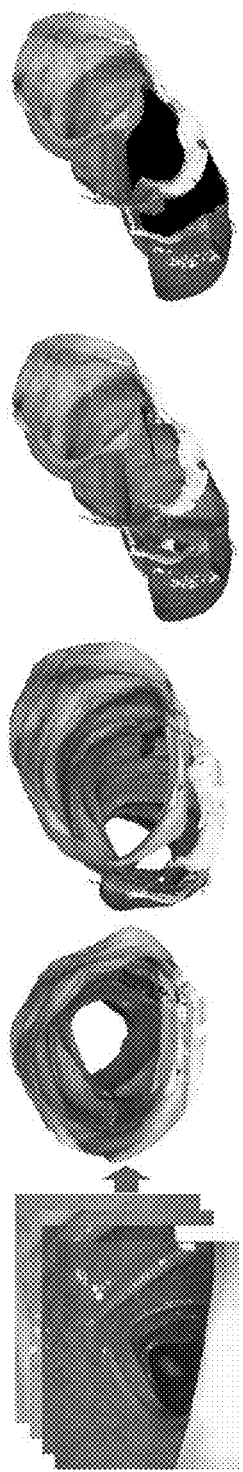
FIG. 1 illustrates a three-dimensional (3D) reconstruction for visualization of missing regions that are occluded by haustral ridges.

Colorectal cancer is the third most common cancer in men and the second in women worldwide [5]. Colonoscopy is an effective method of detecting and removing premalignant polyps and can thus reduce the incidence of subsequent colon cancers. Evidence from multiple studies supports the assertion that polyps and adenomas of all kinds are missed at colonoscopy (pooled miss-rate 22% [7]). One reason for missing polyps and adenomas is that the colonic mucosal surface is not entirely surveyed during a colonoscopy [4]. However, it is very difficult to detect missing colon surface from video alone, let alone quantify its extent, because one sees only a tiny fraction of the colon at any given time rather than a more global view. FIG. 1 illustrates 3D reconstruction 100 for visualization of missing regions that are occluded by haustral ridges (e.g., highlighted by black in the last image).

One solution in accordance with various aspects described herein involves building a system to visualize missing colon surface area by reconstructing the streaming video into a fully interactive dense 3D textured surface that reveals holes in the surface if regions were not visualized. In some embodiments, the system may generate a fully interactive dense 3D textured surface in real-time so that the endoscopist can be alerted of the unseen surface in a timely manner.

Hong et al. [3] used haustral geometry to interpolate virtual colon surface and find missing regions. However, their work only provided single-frame reconstruction and haustral occlusion (without fusion) which is inadequate to determine what has been missed during the procedure. Also, there is no inter-frame odometry being used which could boost reconstruction accuracy.

Some SLAM [6, 1, 2] and Structure-from-Motion (SfM) methods [8] take a video as input and generate both 3D point positions and a camera trajectory. For example, SLAM methods may utilize one or more algorithms from a class of algorithms that construct or update a map of an unknown environment while simultaneously estimating the pose of the camera capturing the frames. However, besides the fact that most of them do not generate dense reconstructions, they work poorly on colonoscopic images for the following reasons: 1) colon images are very low-textured, which disadvantages feature-point-based methods, e.g., ORB-SLAM [6]; 2) photometric variations (caused by moving light source, moist surface and occlusions) and geometric distortions make tracking (predicting camera pose and 3D point positions for each frame) too difficult; and 3) lack of translational motion and poor tracking leads to severe camera/scale drift (shown in FIG. 2) and noisy 3D triangulation.

Convolutional neural networks (CNN) are feed forward neural networks that generally consider only current input (not current input and prior input like RNNs). CNNs have been used for SLAM tasks and predicting dense depth maps [14, 11, 13]. However, these end-to-end networks are subject to accumulated camera drift because there is no optimization used during prediction as in standard SLAM systems. In contrast, there are works that use CNN to improve a standard SLAM system [10, 12]. CNN-SLAM [10] incorporated CNN depth prediction to the LSD-SLAM [2] pipeline to provide robust depth initialization. The dense depth maps are finally fused into a global mesh. Yang et al. [12] used CNN-predicted depth (trained on stereo image pairs) to solve the scale drift problem in DSO [1]. However, there are neither stereo images nor groundtruth depth for colonoscopic images. Also, training a CNN on colonoscopic images is difficult for the aforementioned challenges.

Figure 2:
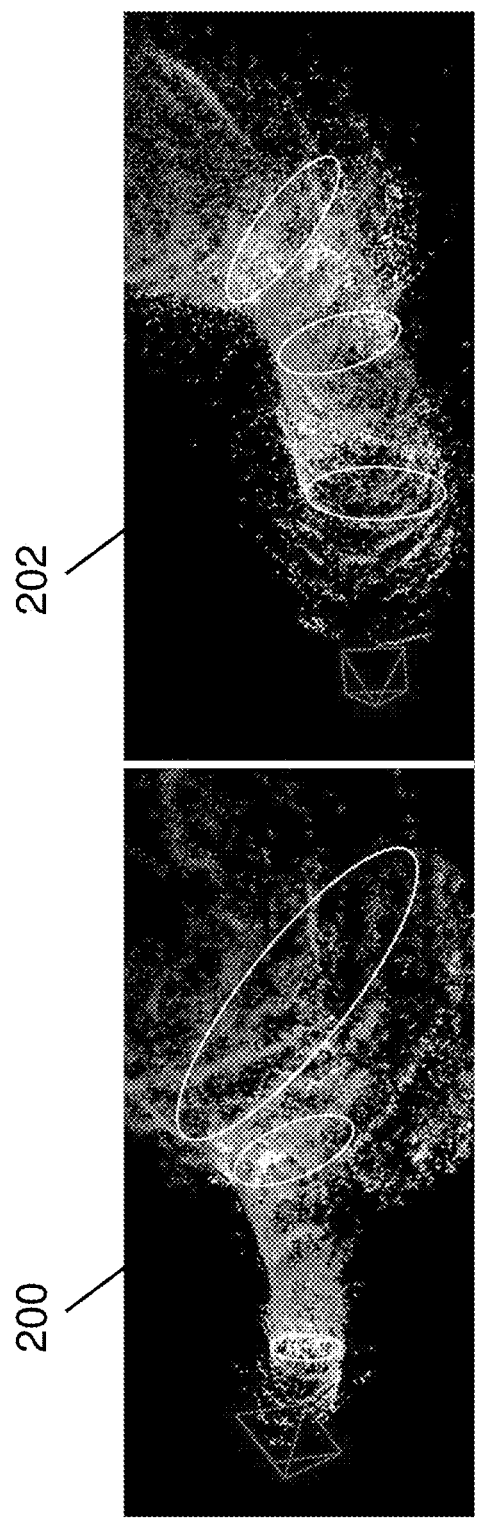
FIG. 2 illustrates two sparse points clouds generated by different simultaneous localization and mapping (SLAM) systems.

FIG. 2 illustrates two sparse points clouds 200 (left image) and 202 (right image) generated by different SLAM systems. Sparse point cloud 200 is produced by a Direct Sparse Odometry (DSO) SLAM pipeline [1] using a chunk of colonoscopy video. Sparse point cloud 202 is produced by an example deep-learning-driven SLAM system using the same chunk of colonoscopy video. The cross sections are approximated by white ellipses. The diameters of the cross sections in sparse point cloud 200 are dramatically decreasing (scale drift), which is non-realistic. In contrast, the diameters of the cross sections in sparse point cloud 202 are much more consistent in scale because of depth maps predicted by an RNN used by the deep-learning-driven SLAM system.

Various embodiments of a deep-learning-driven SLAM system are described herein. For example, an example deep-learning-driven SLAM system may use a trained RNN to predict both depth and camera poses and combine the predicted output in a novel fashion with a SLAM pipeline to improve the stability and drift of successive frames' reconstructions. The RNN training addresses various difficulties of colonoscopic images. The SLAM pipeline optimizes the depth and camera poses provided by the RNN. Based on the optimized camera poses, the depth maps of the keyframes are fused into a textured global mesh using a nonvolumetric method. In this example, the SLAM system may run in real-time or near real-time and may produce a high-quality camera trajectory and colon reconstruction which can be used for missed region visualization in colonoscopy.

Methodology

Full Pipeline

Figure 3:
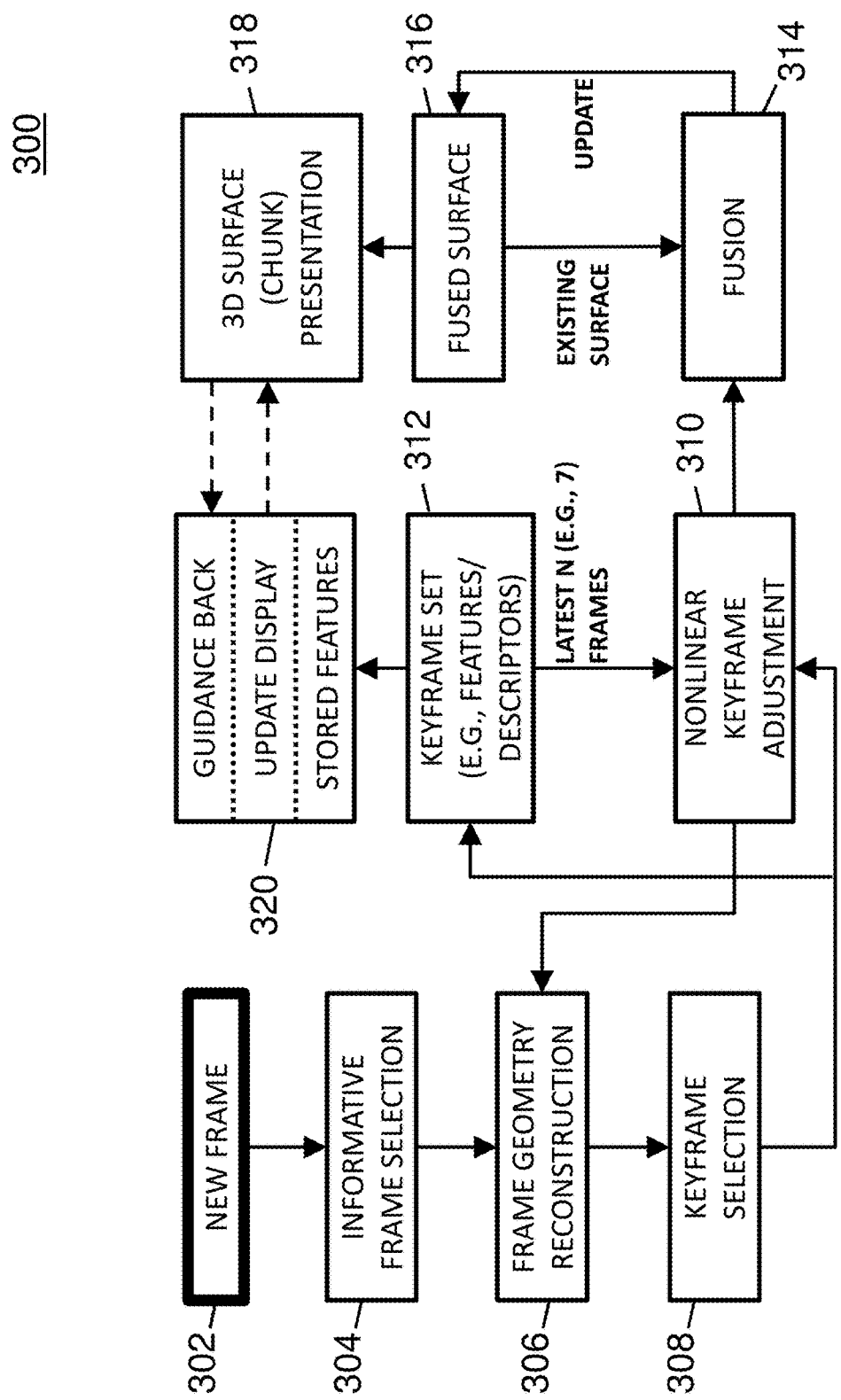
FIG. 3 is a diagram illustrating a processing method associated with an example deep-learning-driven SLAM system.

FIG. 3 is a diagram illustrating a processing method 300 associated with an example deep-learning-driven SLAM system. In some embodiments, method 300 may be performed successively in real-time (or near real-time) to the video frames as they are captured by the colonoscope.

Referring to FIG. 3, a new video frame captured by a colonoscope during a colonoscopy may be received by a deep-learning-driven SLAM system (302). For example, a video frame may be a single two dimensional (2D) image in a video sequence. In this example, a colonoscopy video at 30 frames per seconds (fps) captures about 10,000 frames during the colonoscope withdrawal. If the colon is 1.5 meters long, there are about 7 frames per linear millimeter.

The frame may be analyzed to determine whether the frame is informative (e.g., clear and not redundant) or non-informative (304). If deemed non-informative, the frame may be ignored. For example, an informative frame may show enough area of the colon wall with clarity to support 3D reconstruction. In contrast, an uninformative frames may be too blurry, too interrupted by water or fecal material, or too close to the colon wall to be useful. Based on studied colonoscopic videos, about 50% of all frames were found to be uninformative.

In some embodiments, specularity removal may be performed on frames during or before informative frame selection. Specular points are very common in endoscopic videos because the light source is very close to the tissue surface. Moreover, because the surface is moist, the specularities are quite intense. Specularity causes problems in 3D reconstruction, including incorrect feature detection and matching and saturated shading information.

In some embodiments, various frame processing analysis aspects may be performed by a neural network. For example, informative frame selection and/or specularity removal may be performed by one or more trained CNNs or RNNs.

If the frame is deemed informative, a trained RNN may compute the camera pose and the "geometry" (e.g., depth map(s)) of the colon surface depicted in that frame for each of the frame's pixels (306). For example, a computed camera pose may include the location and orientation of the camera relative to the previous keyframe.

The computed (estimated) geometry is aligned with a previous frame using the computed camera pose, and the result is evaluated for geometric and texture consistency and non-redundancy (e.g., adequate camera motion) with those of recent previous frames. If the frame is deemed redundant, the frame may be ignored. If it is inconsistent but not part of a multi-frame sequence of inconsistent frames, it is ignored. Otherwise, if the frame is consistent, the frame is deemed a keyframe usable for reconstructing a 3D textured structure (308).

In some embodiments, determining too many successive frames (e.g., based on a threshold value) are inconsistent may act as a trigger for indicating the end of a colon chunk (e.g., a 3D reconstructed colon portion) and the potential start of a new colon chunk. For example, a chunk may be 10-20 centimeters long.

The keyframe's pose, geometry, and texture may be adjusted to limit drift and to optimize the dense geometry and the camera pose using the latest N (e.g., 7) frames (310).

After keyframe selection, the keyframe may be added to a keyframe set (312). For example, a keyframe set may include a certain number of latest keyframes (e.g., the most recent seven) and may be used to provide input for various optimization techniques. The keyframe set may also be analyzed (e.g., during a fusion process) to identify descriptors and/or features (e.g., unique places in the colon) in the keyframes which may be useful for guiding back an endoscopist to missed regions of a colon chunk.

The adjusted keyframe may be incrementally fused (e.g., with an existing surface or prior adjusted keyframe) into a chunk of the colon (314), producing a 3D textured surface of that portion of the viewed colon (316). During the fusion process, regions within the chunk that were not reconstructable may be identified and the size of these regions may be calculated. Also, during the fusion process, features may be identified and stored to allow later guidance back to the non-reconstructable regions since features can provide a means of frame-to-frame correspondence. For example, a feature may include a location in a frame or surface that is centered in a small region that contains multiple recognizable attributes such as color or intensity gradients.

In some embodiments, various feature extraction and/or analysis aspects may be performed by a neural network. For example, feature selection (e.g., during mesh fusion) may be performed by a trained CNN.

The chunk may be presented via a display to the endoscopist (318). The display may highlight the size of those regions that were not reconstructed (e.g., not captured by the camera), and may alert the endoscopist if the size of the missing regions is larger than some threshold.

If the endoscopist chooses to return to view those unreconstructed regions, the system may provide guidance back to those regions (320). In some embodiments, the system may provide guidance back by calculating features from the video on the way back and comparing them against the stored chunk features. In such embodiments, the system may use the comparison to show on the display where the colonoscope is located relative to the present chunk and/or the previous chunk.

In some embodiments, upon arriving at a previously unseen region, the endoscopist may be guided to each location previously unseen, and when each location is visualized, the reconstructions of that region may be fused with the previous reconstructions.

In some embodiments, an example deep-learning-driven SLAM method may include the following steps: deep-learning-driven tracking (e.g., predicting frame-wise depth map and tentative camera pose which are used to initialize the photoconsistency-based tracking); keyframe selection (e.g., upon enough camera motion, creating a new keyframe as the new tracking reference and updating the neural network); local windowed optimization (e.g., jointly optimizing camera poses and sparsely sampled points' depth values of the latest N (e.g., 7) keyframes); marginalization (e.g., finalizing the oldest keyframe in a window so that the keyframe is marginalized from the optimization system); and fusion (e.g., using optimized camera pose, fusing the image and the depth map of the marginalized keyframe with the existing surface).

Deep-Learning-Driven Tracking

Deep learning represents one or more machine learning artificial intelligence (AI) techniques that use multi-layer neural networks for classification and regression. When properly trained and/or configured, AI can perform some non-trivial tasks more quickly than traditional geometric methods. Some deep learning techniques may involve the use of one or more neural networks, e.g., CNNs or RNNs.

In some embodiments, deep-learning-driven tracking may involve using an enhanced RNN for depth and pose estimation (eRNN-DP) which predicts a depth map and a camera pose for each image or frame in the video. It is important to note that original RNN-DP [11] cannot be directly trained on colonoscopic videos because there is no groundtruth depth available. In addition, the pose estimation network in original RNN-DP is trained based on image reprojection error, which is severely affected by the specular points and occlusions in colonoscopic videos. Therefore, in this section, new strategies are discussed for successfully training an eRNN-DP on colonoscopic videos. In order solve the problem of the lack of groundtruth depth, SfM [8] was used to produce a sparse depth map for each individual colonoscopic video frame. These sparse depth maps were then used as groundtruth for eRNN-DP training. Sixty colonoscopy videos were used, where each video contains about 20,000 frames. Every 200 consecutive frames were grouped into a subsequence with an overlap of 100 frames with previous subsequence. Hence, 12,000 subsequences were generated from the sixty colonoscopic videos. Then SfM [8] used all the subsequences to generate sparse depth maps for each frame. Following the training pipeline in RNN-DP [11], these sparse depth maps are used as groundtruth for training.

To avoid the error from specularity (saturation), a specularity mask $M_{spec}^t$ may be computed for each frame based on an intensity threshold. Image reprojection error at saturated regions may be explicitly masked out by $M_{spec}^t$ during training.

Colonoscopic images may also include severe occlusions by haustral ridges, so a point in one image may not have any matching point in other images. Original RNN-DP [11] did not handle occlusion explicitly. In order to properly train an enhanced RNN-DP on colonoscopic video, an occlusion mask $M_{occ}^t$ may be computed to explicitly mask out image reprojection error at occluded regions. In some embodiments, an occlusion mask may be determined by a forward-backward geometric consistency check, which was introduced in [13].

In some embodiments, the eRNN-DP described herein or a similar network may output frame-wise depth maps and tentative camera poses (e.g., relative to the previous keyframe). The outputs may be used to initialize the photoconsistency-based tracking [1] that refines the camera pose.

Keyframe Management and Optimization

In some embodiments, an example deep-learning-driven SLAM system may store a history of all keyframes. The latest keyframe may be used as the tracking reference for the incoming frames. During keyframe selection, if the relative camera motion or the change of visual content (measured by photoconsistency) is large enough, the new frame may be deemed informative and/or a keyframe and be inserted into the keyframe set. The frame may also be used as a new tracking reference.

When a keyframe is inserted, a nonlinear keyframe adjustment process, also referred to herein as a local adjustment bundle process, may be triggered. The local window may include the latest 7 keyframes. From each of these keyframes, 2000 2D active points may be sampled in total preferring high-gradient regions. Each active point may be based on exactly one keyframe but is projected to other keyframes to compute a photometric error. By minimizing the total photometric loss, the camera poses (7×6 parameters) and the depth values of the sampled points (2000 parameters) may be jointly optimized. In addition, to tolerate global brightness change of each keyframe, two lighting parameters per frame may be added to model the affine transform of brightness. One purpose of the sampling is to enable efficient joint optimization by maintaining sparsity.

After optimization, the oldest keyframe may be excluded from the optimization system by marginalization based on Schur complement [1]. The finalized reconstructed keyframe may be fused into the global mesh.

In some embodiments, an example deep-learning-driven SLAM system may be enhanced using an eRNN-DP network or another neural network. In a keyframe selection process, when a new keyframe is established, an original DSO based system uses the dilated projections of existing active points to set the depth map for this keyframe, which is used in the new tracking tasks. The resulting depth map is sparse, noisy and are subject to scale drift. In contrast, the deep-learning-driven SLAM system may set the depth map for this keyframe using depth prediction from an eRNN-DP. Such depth maps are dense, more accurate and scale consistent. It also makes the SLAM system easier to bootstrap, which is known to be a common problem for SLAM. On the other hand, the SLAM system also improves the result of raw eRNN-DP predictions by optimization, which is very important to eliminate accumulated camera drift of RNN-DP. AS such, this combination of eRNN-DP and DSO provides synergy and is a win-win strategy.

As stated above, a trained eRNN-DP network may be integrated into a DSO based SLAM system. Its execution is directed by the keyframe decisions made by the system. After tracking, the hidden states of the RNN-DP remain at the stage of the latest keyframe. They are updated only when a new keyframe is inserted.

Fusion into a Chunk

In some embodiments, independent depth maps predicted by an RNN-DP or other neural network may be fused into a global mesh (e.g., a 3D surface). In some embodiments, a point-based (nonvolumetric) method called SurfelMeshing may be used to fuse the independent depth maps predicted by an RNN-DP into a global mesh [9]. In such embodiments, the RNN-DP may take an RGB (video)+depth+camera_pose sequence as input and may generate a 3D surface. A surfel is a point-based computer graphics primitive used to render 3D scenes. It is highly scalable and efficient and is parallelizable on a GPU. However, SurfelMeshing needs temporally consistent depth maps to perform the fusion. Since SurfelMeshing requires well-overlapped depth maps, a preprocessing step may be used to further align the depths.

In some embodiments, e.g., when using SurfelMeshing to create a global mesh, a geometric consistency loss value may be used during RNN training, where the geometric consistency loss value may explicitly impose temporal consistency among predicted depth maps. In such embodiments, the geometric consistency loss value may be used to avoid or minimize a computationally expensive post-processing step. The idea is for each predicted depth map (target) to project it onto every neighboring frames (sources) using the estimated relative camera poses. Then the projected target depth map is compared to the estimated depth map of the source frame that being projected to. If the estimations are temporally consistent, then the projected target depth maps will be the same or very close to the depth maps of the corresponding source frames. This geometric consistency loss is mathematically defined as $$L_{dc} = \sum_{t=0}^{N} \sum_{i=0}^{t} \sum_{\Omega} \lambda_t^i \omega_t^i |\hat{Z}_t^i - Z_i| \quad (1)$$

where is the projected depth map of the $i^{th}$ view's onto the $i^{th}$ view. $\omega_t^i$ is a binary mask indicating whether a pixel of $\hat{Z}_t^i$ has a counterpart in $Z_i$, and $\lambda_t^i$ is a weighting term that decays exponentially based on t–i.

In some embodiments, window depth averaging may be performed during fusion processing. For example, during fusion processing, an example deep-learning-driven SLAM system may use a temporal window that keeps the latest 7 marginalized keyframes. In parallel, the depth map of the 6 old keyframes may first be projected to the latest keyframe. Second, the new keyframe may replace its depth with the weighted average of the projected depth maps and its current depth. The weights may be inversely proportional to time intervals. The average depth may be used for fusion. Window depth averaging may effectively eliminate the non-overlapping between depth maps at a cost of slight smoothing.

Concurrently with fusing successive depth maps into a mesh, SurfelMeshing or a variation thereof may involve texturizing the mesh using one or more techniques. For example, a number of texture maps derived from various frames of an endoscopic video that indicate texture but avoid dramatic color differences caused by various issues (e.g., illumination (light binding with camera), reflection, and surface deformation). In this example, texture fusion may involve an iterative process for fusing the texture maps acquired from different views to create a seamless texture. In some embodiments, a fusion result (a 3D textured mesh) may be used for missing region visualization and potentially for region measurement.

Experiments

A tested deep-learning-driven SLAM system was able to reconstruct a colon in chunks when the colon structure is clearly visible. The end of a chunk was determined by recognizing a sequence of low quality frames, e.g., frames of garbage or bad lighting, whose tracking photoconsistencies are all lower than a threshold. The chunks reconstructed were able to visualize the missing regions. Quantitative results are provided for estimating the trajectory accuracy and qualitative results on the reconstruction and missing region visualization.

Trajectory Accuracy

To evaluate the trajectory accuracy, the tested deep-learning-driven SLAM system (referred to herein as 'our method') is compared to DSO [1] and RNN-DP [11]. Since there is no groundtruth trajectory for colonoscopic video, to generate high quality camera trajectories in an offline manner, we use colmap [8], which is a state-of-the-art SfM software that incorporates pairwise exhausted matching and global bundle adjustment. These trajectories are then used as "groundtruth" for our evaluation.

Evaluation Metrics

The absolute pose error (APE) is used to evaluate global consistency between the real-time system estimated and the colmap generated "groundtruth" trajectory. We define the relative pose error $E_i$ between two poses $P_{gt,i}, P_{est,i} \in SE(3)$ at timestamp i as $$Ei = (P_{gt,i})^{-1} P_{est,i} \in SE(3) \quad (2)$$

The APE is defined as:

$$APE_i = \|trans(E_i)\| \quad (3)$$

where $trans(E_i)$ refers to the translational components of the relative pose error. Then, different statistics can be calculated on the APEs of all timestamps, e.g., the RMSE:

$$RMSE = \sqrt{\frac{1}{N} \sum_{i=1}^{N} APE_i^2} \quad (4)$$

TABLE 1

Average statistics based on the APE across twelve colonoscopic sequences.

| Method | RMSE | STD | MIN | MEDIAN | MEAN | MAX |
|---|---|---|---|---|---|---|
| RNN-DP | 0.617 | 0.253 | 0.197 | 0.518 | 0.560 | 1.229 |
| DSO | 0.544 | 0.278 | 0.096 | 0.413 | 0.465 | 1.413 |
| OURS | 0.335 | 0.157 | 0.074 | 0.272 | 0.294 | 0.724 |

Figure 4A:
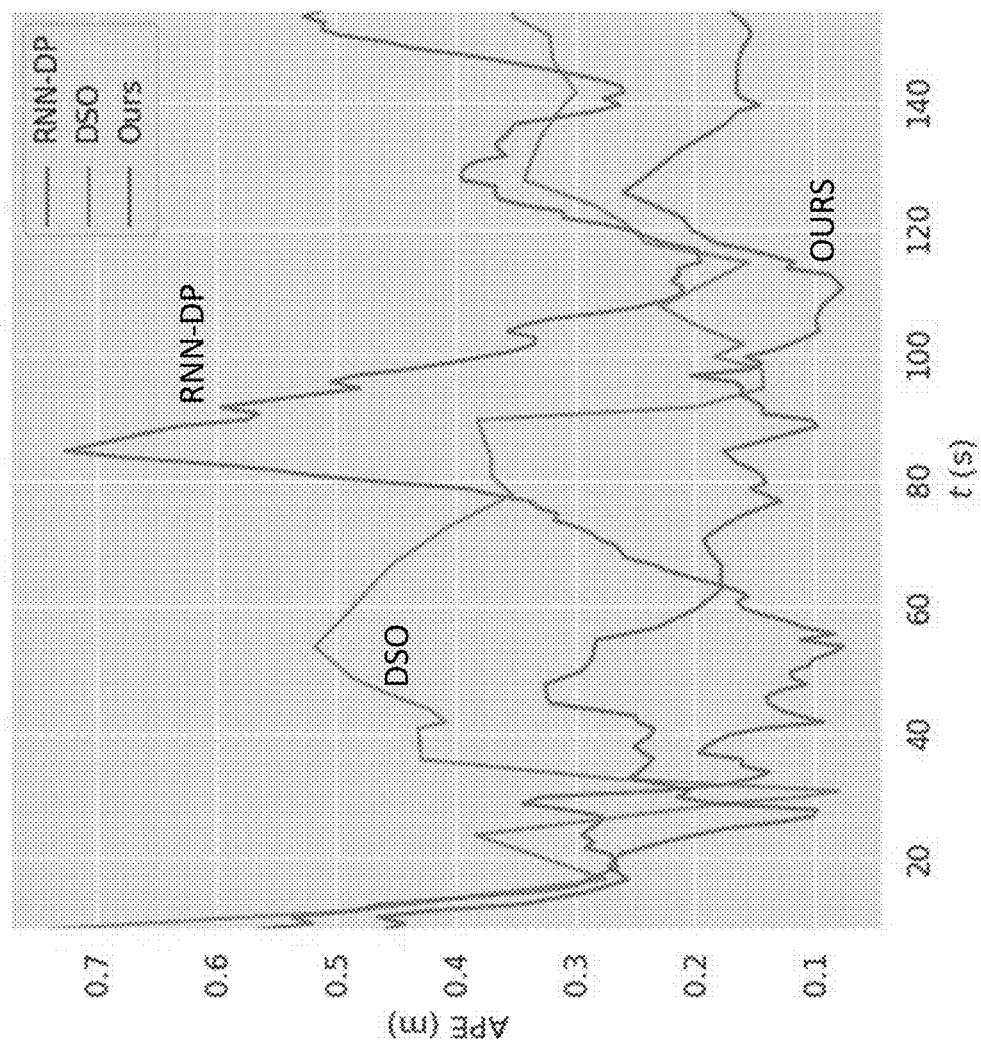
FIGS. 4A-4C shows evaluation results using different techniques or systems.
Figure 4B:
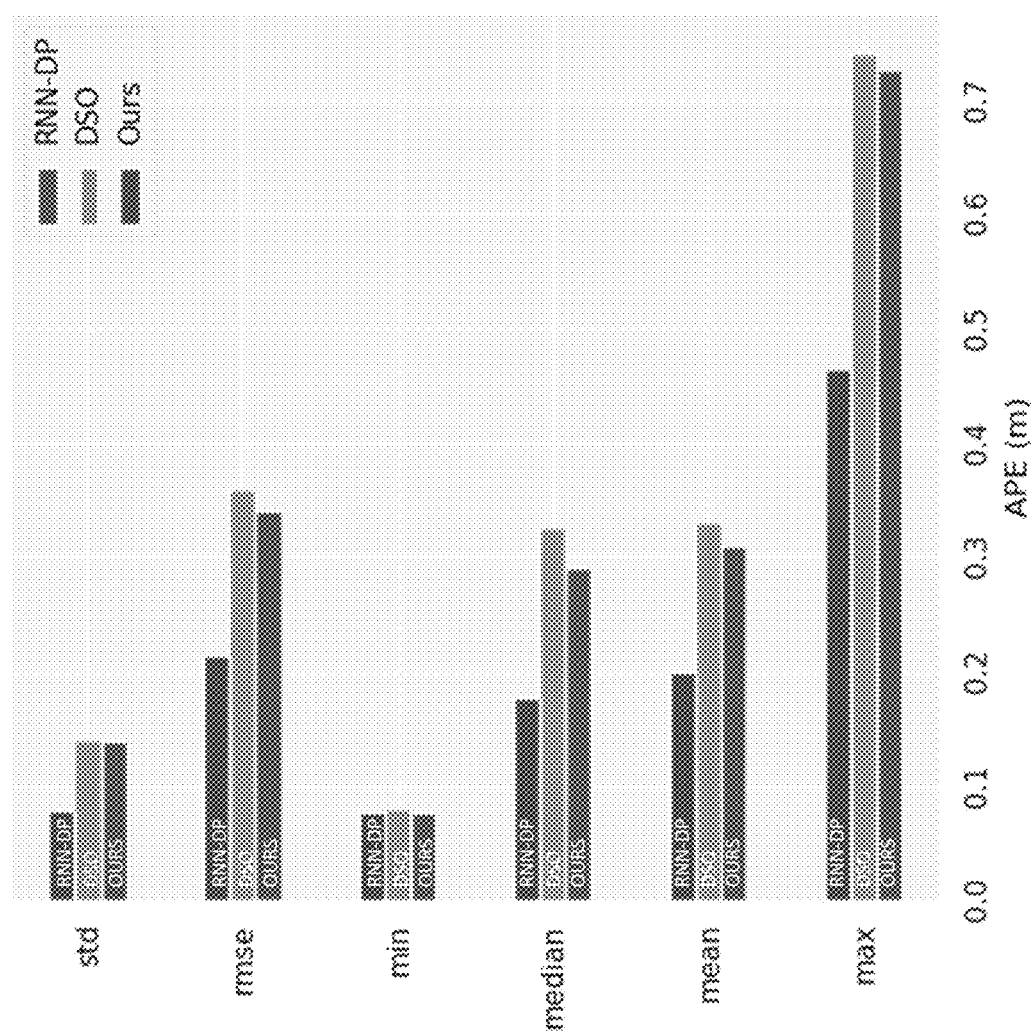
Figure 4C:
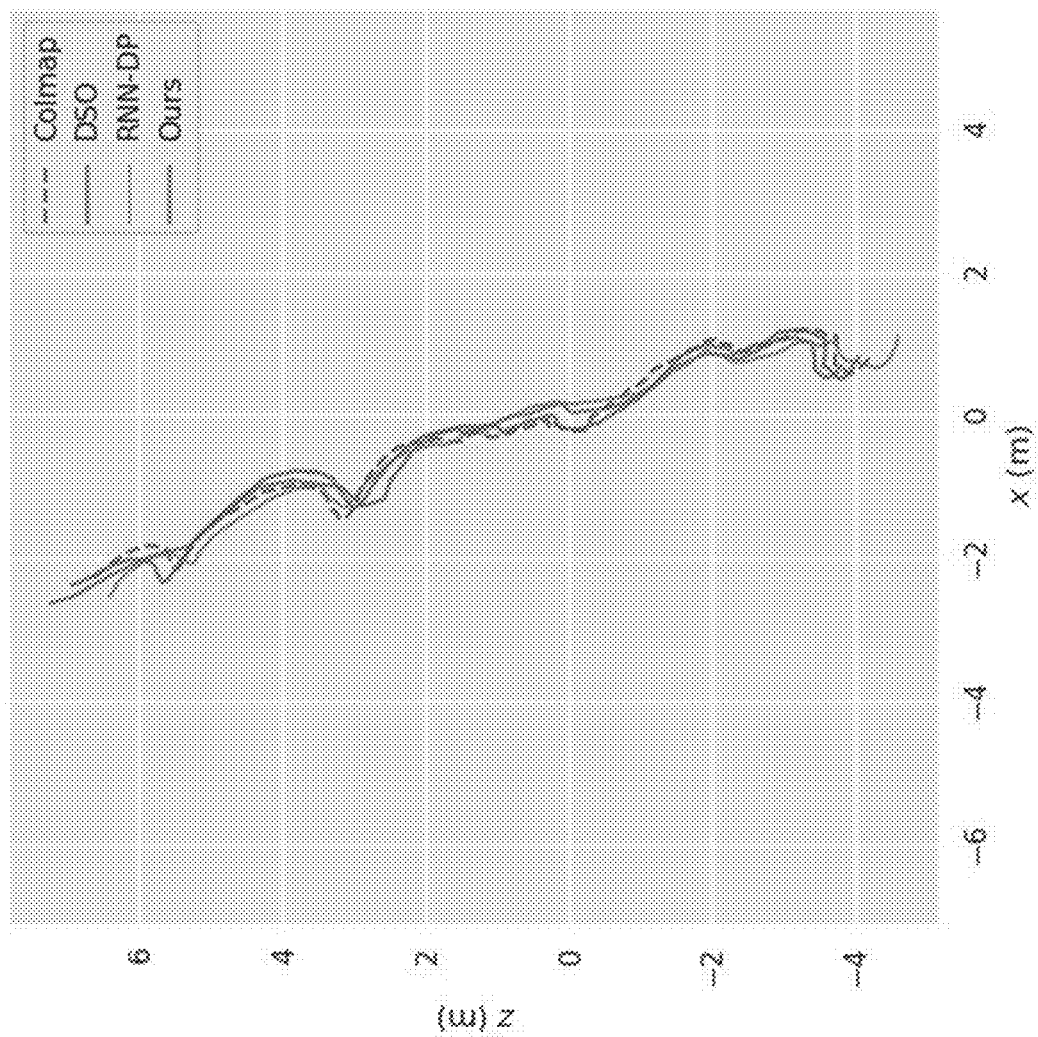

FIGS. 4A-4C show evaluation results on one colonoscopic sequence. FIG. 4A includes diagram 400 depicts the absolute pose error (APE) of the three approaches on an example sequence. As shown in diagram 400, our method has the lowest APE at most times. FIG. 4B includes diagram 402 depicts APE statistics of the three approaches. As shown in diagram 402, our method is significantly better than the other two approaches. FIG. 4C includes diagram 404 depicts the trajectories of the three approaches together with the groundtruth. Table 1 shows the statistics of FIG. 4B but averaged across twelve colonoscopic sequences. As indicated in Table 1, our method achieves the best result on all the metrics.

Reconstructions and Missing Regions

Figure 5:
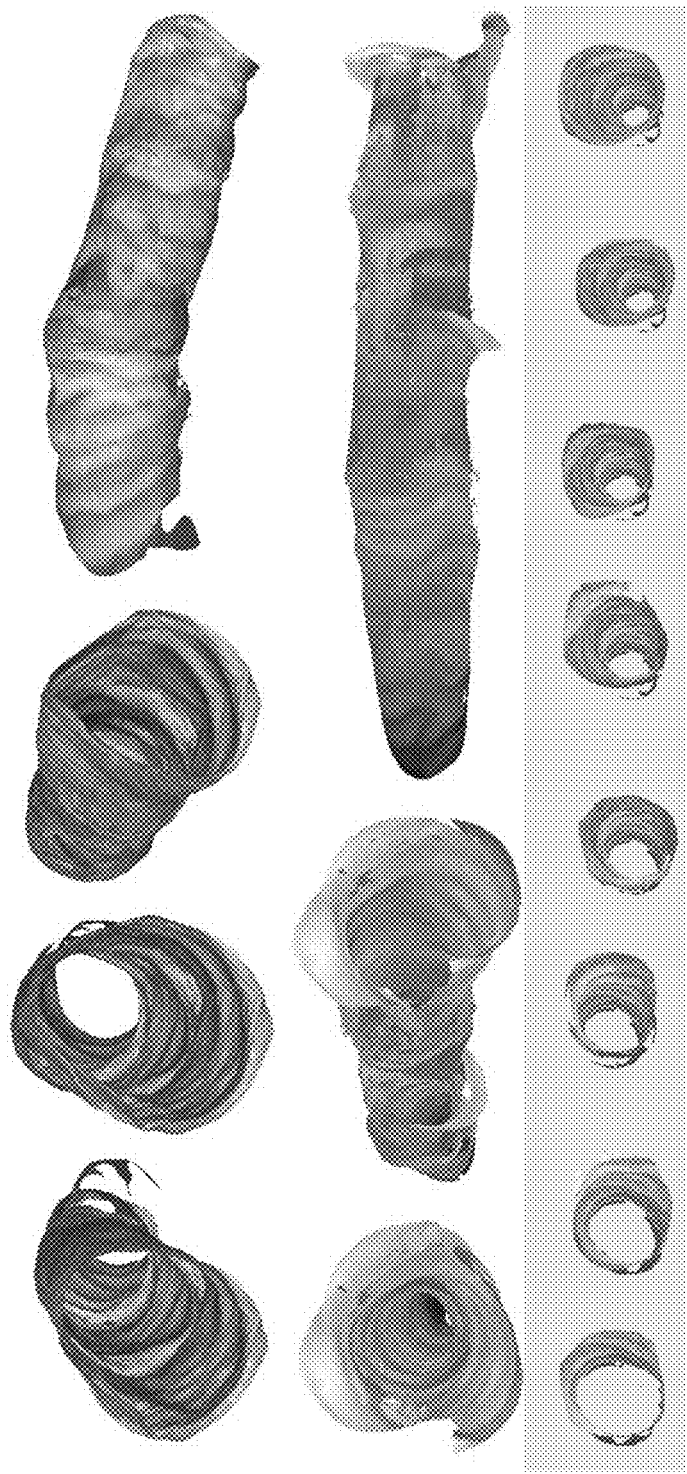
FIG. 5 shows colon chunks from multiple points of view.

FIG. 5 shows colon chunks from multiple points of view. Each of row 1 and row 2 in FIG. 5 shows the reconstruction of a colon chuck for multiple points of view. Row 3 shows an incremental fusion of the row 1 example.

Figure 6:
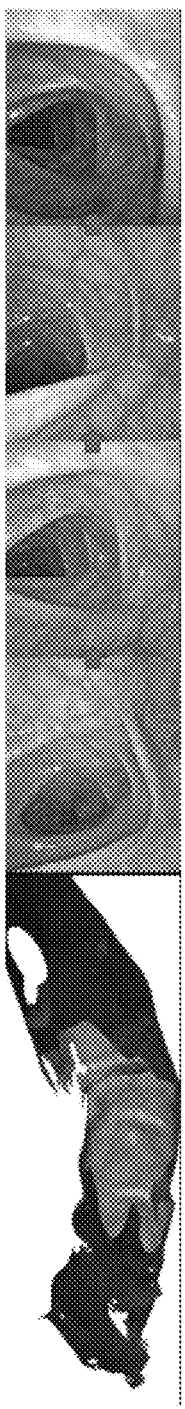
FIG. 6 shows a 3D reconstruction of a colon chunk with missing portions due to the lack of camera orientations.

FIG. 6 shows a 3D reconstruction of a colon chunk with missing portions due to the lack of camera orientations.

There may be multiple reasons for missing regions. Two notable ones are lack of camera orientations to the full circumference of parts of a colon and haustral ridge occlusion. While missing regions may be verified by checking respective video frames (the upper part of the colon was not seen), missing regions might not be realized during a colonoscopy.

Figure 7:
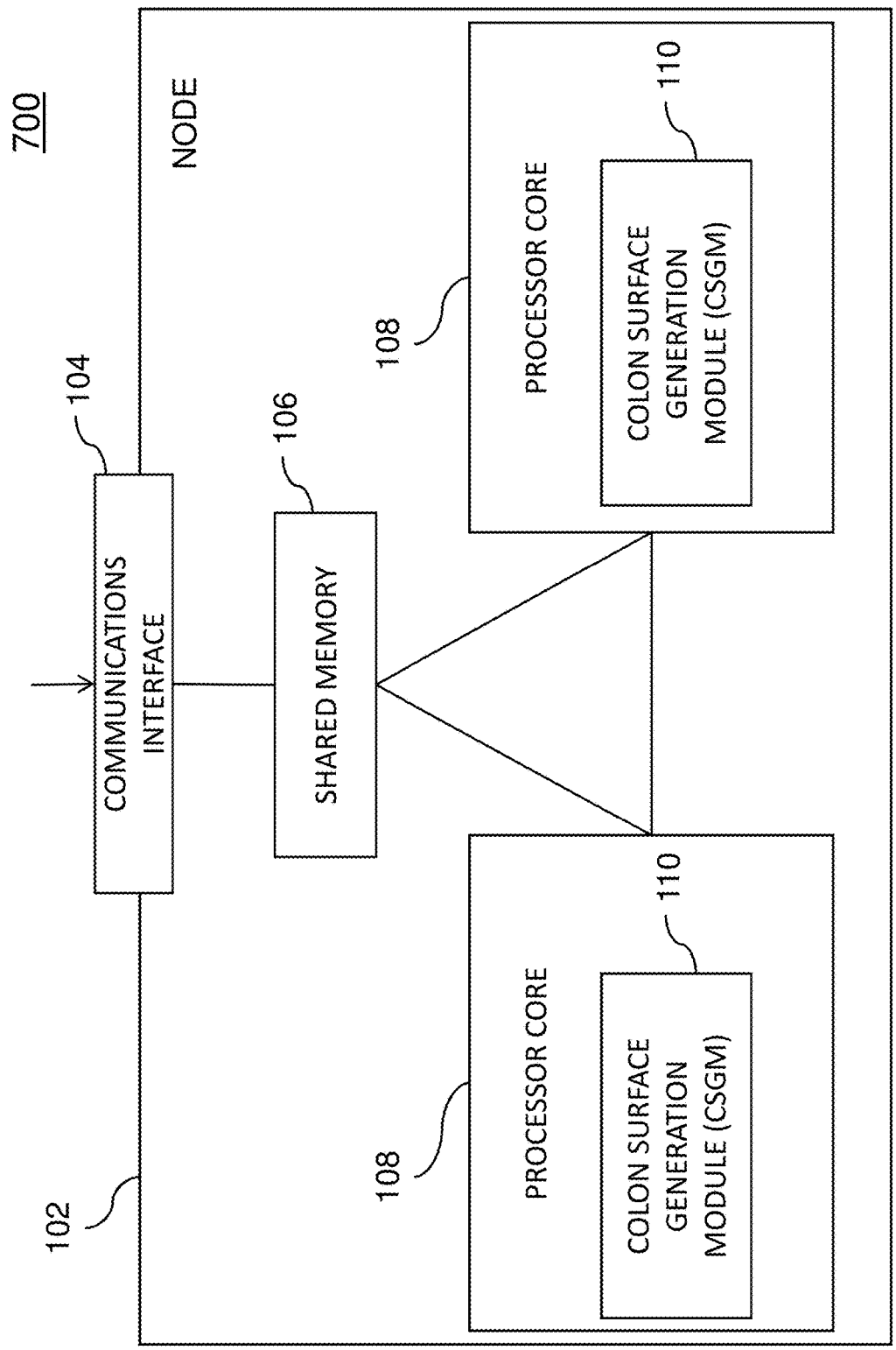
FIG. 7 is a diagram illustrating an example node for 3D reconstruction of colon surfaces.

FIG. 7 is a diagram illustrating an example node 102 (e.g., one or more single or multiple processing core computing devices) for 3D reconstruction of colon surfaces for determining missing regions. Node 102 may be any suitable entity, such as one or more computing devices or platforms, for performing one more aspects of the present subject matter described herein. In some embodiments, components, modules, and/or portions of node 102 may be implemented or distributed across multiple devices or computing platforms.

Node 102 may include a communications interface 104, a shared memory 106, and one or more processor cores 108. Communications interface 104 may be any suitable entity (e.g., a communications interface, a network interface card, and/or a data acquisition and generation (DAG) card) for receiving and/or sending messages. For example, communications interface 104 may be interface between various nodes 102 in a computing cluster. In another example, communications interface 104 may be associated with a user interface or other entity and may receive configuration settings and/or source data, such as colonoscopic video, for deriving a 3D textured colon surface from colonoscopic video and/or for interacting with the 3D textured colon surface.

In some embodiments, communications interface 104 or another component may be configured to identify or select a processor core 108 for processing, analysis, and/or storage. For example, communications interface 104 may receive information from another node in a cluster and may determine that a particular processor core 108 should process the received information. In another example, communications interface 104 may store information in shared memory 106 and the stored information may be retrieved later by an available processor core 108.

Shared memory 106 may be any suitable entity (e.g., random access memory or flash memory) for storing 3D textured surface modeling information, registration algorithms, surface reconstruction algorithms, specularity removal algorithms, texture fusion algorithms, colonoscopic videos, and/or other information. Various components, such as communications interface 104 and software executing on processor cores 108, may access (e.g., read from and/or write to) shared memory 106.

Each of processor cores 108 represents any suitable entity (e.g., a physical processor, a field-programmable gateway array (FPGA), and/or an application-specific integrated circuit (ASIC)) for performing one or more functions associated with RNN training, SLAM processing, 3D surface reconstruction, frame preprocessing, frame selection, seamless texture fusion, and/or related methods, algorithms, and/or techniques. Processor cores 108 may be associated with a colon surface generation module (CSGM) 110. For example, CSGM 110 or software therein may be executable by one or more processor cores 108.

CSGM 110 may be configured to use one or more methods, algorithms, and/or techniques for deriving or reconstructing a 3D colon surface in real-time or near real-time. For example, CSGM 110 may utilize one or more deep learning techniques and/or related networks (e.g., RNNs, CNNs, etc.) to generate a 3D colon surface from a plurality of video frames of a colonoscopic video. In this example, CSGM 110 or related entities may perform video frame preprocessing to identify a plurality of keyframes of a colonoscopic video, wherein the video frame preprocessing includes informative frame selection and keyframe selection. CSGM 110 or related entities may also generate, using a recurrent neural network and direct sparse odometry, camera poses and depth maps for the keyframes. CSGM 110 or related entities may then fuse, using SurfelMeshing, the camera poses, and the depth maps, keyframes into a three-dimensional (3D) surface of a colon portion, wherein the 3D surface indicates at least one region of the colon portion that was not visualized.

In some embodiments, various functions described herein and/or related neural networks may utilize highly parallel computers or processors, such as GPUs. For example, a trained neural network (e.g., a CNN or an RNN) may be deployed using a machine learning software package, e.g., Tensorflow. In this example, the trained neural network can use multiple cores of a CPU or GPU to perform parallelizable computational tasks.

CSGM 110 may be configured to use one or more methods, algorithms, and/or techniques for allowing a user (e.g., an endoscopist) to interact with a 3D colon surface in real-time or near real-time. For example, CSGM 110 may use a display to guide an endoscopist back to a missed region of the colon portion (e.g., a non-visualized region). In this example, CSGM 110 may guide the endoscopist by comparing features in a current video (e.g., video while the colonoscope is moving toward to the missed region) and stored features identified when the colon chunk was initially viewed. As the colonoscope gets closer to the missed region (e.g., based on feature matching), CSGM 110 may provide text prompts and/or graphics via the display or other indicators (e.g., audio) so that the endoscopist will slow down and/or rotate the colonoscope to view the missed region.

Additional details regarding various techniques capable of being performed by CSGM 110, processor core(s) 108, node 102, and/or another node or module are described in U.S. patent application Ser. No. 16/241,356, filed Jan. 7, 2019; the disclosure of which is incorporated herein by reference in its entirety.

It will be appreciated that FIG. 7 is for illustrative purposes and that various nodes, their locations, and/or their functions may be changed, altered, added, or removed. For example, some nodes and/or functions may be combined into a single entity. In a second example, a node and/or function may be located at or implemented by two or more nodes.

Figure 8:
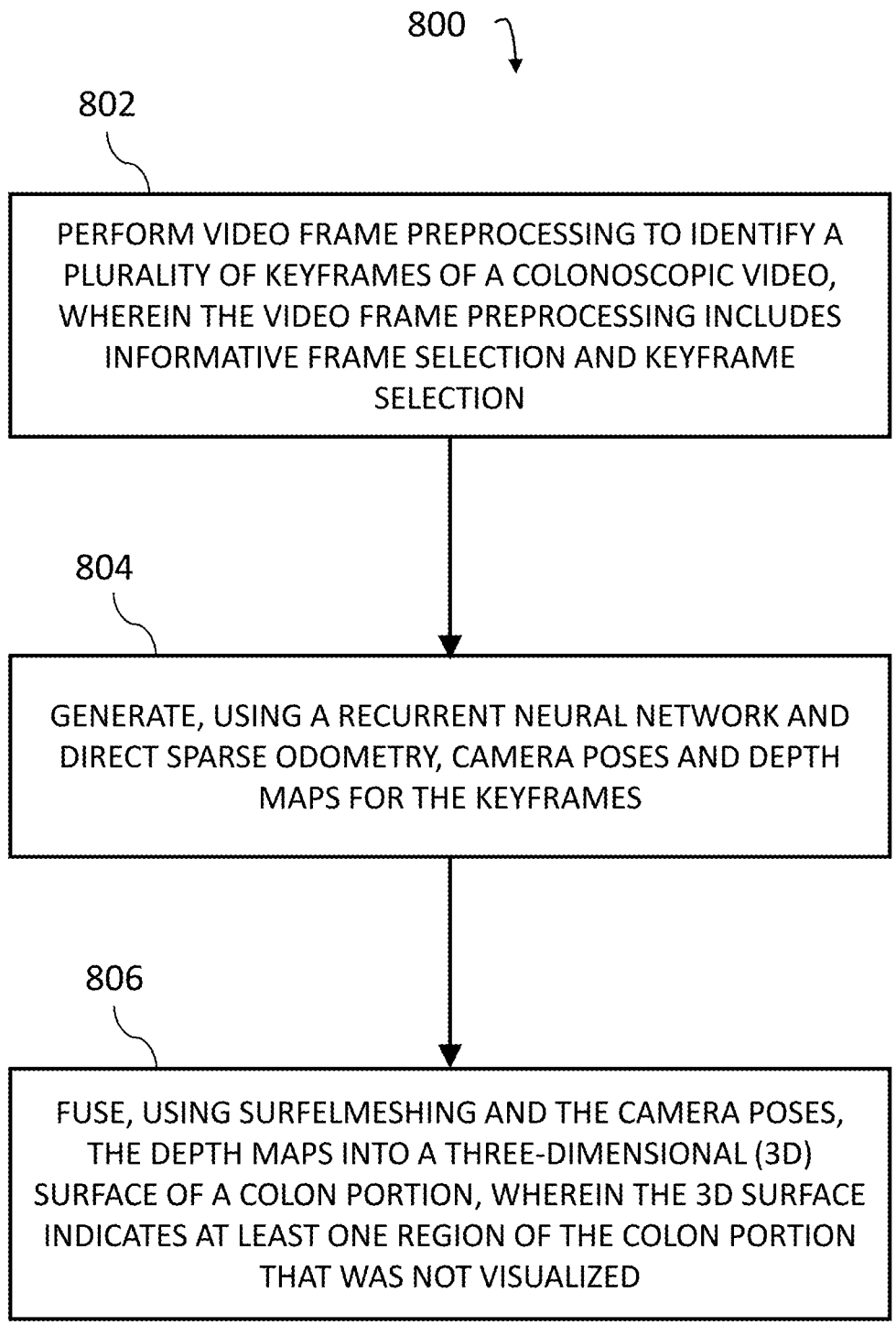
FIG. 8 is a diagram illustrating an example process for 3D reconstruction of colon surfaces.

FIG. 8 is a diagram illustrating an example process 800 for 3D reconstruction of colon surfaces. In some embodiments, example process 1700, or portions thereof, may be performed by or at CSGM 110, processor core(s) 108, node 102, and/or another node or module.

Referring to FIG. 8, in step 802, video frame preprocessing may be performed to identify a plurality of keyframes of a colonoscopic video, where the video frame preprocessing includes informative frame selection and keyframe selection.

In some embodiments, informative frame selection may be performed using a neural network, e.g., a CNN.

In step 804, camera poses and depth maps for the keyframes may be generated using a recurrent neural network and direct sparse odometry.

In some embodiments, generating camera poses and depth maps for keyframes may include using an RNN (e.g., eRNN-DP) and a number (e.g., 7) of recent keyframes to generate frame-wise depth maps and tentative camera poses and optimizing the tentative camera poses using direct sparse odometry.

In some embodiments, output generated using direct sparse odometry may be used to refine an RNN (e.g., eRNN-DP) for generating improved camera poses.

In some embodiments, an RNN may be trained using a geometric consistency loss value to explicitly impose temporal consistency among depth maps generated by the recurrent neural network.

In some embodiments, an RNN may be trained using video frames from one or more colonoscopic videos and groundtruth depth may be determined using a SfM approach to generate a sparse depth map for each of the video frames.

In some embodiments, an RNN may be trained using a computed specularity mask to mask out image reprojection error at saturated regions in the video frames, wherein the computed specularity mask may be determined for each video frame based on an intensity threshold value.

In some embodiments, an RNN may be trained using a computed occlusion mask to mask out image reprojection error at occluded regions in video frames, wherein the computed occlusion mask may be determined by a forward-backward geometric consistency check.

In step 806, the depth maps may be fused into a 3D surface of a colon portion using SurfelMeshing and the camera poses, where the 3D surface indicates at least one region of the colon portion that was not visualized.

In some embodiments, CSGM 110 or another node or module may be configured for guiding, using a display, an endoscopist back to the at least one region of the colon portion that was not visualized.

In some embodiments, guiding an endoscopist may include comparing features in the colonoscopic video as a colonoscope heads back toward a colon portion that was previously viewed and stored features identified when the colon portion was initially viewed.

In some embodiments, guiding the endoscopist occurs in real-time or near real-time.

It should be noted that, besides colonoscopy, a variety of other clinical uses of endoscopy can benefit from real-time or near real-time reconstruction or at least reconstruction immediately at the end of the endoscopic examination while the patient is still present. The methods described here can be applied to those endoscopies as well.

It should also be noted that CSGM 110, processor core(s) 108, node 102, and/or functionality described herein may constitute a special-purpose computing device. Further, CSGM 110, processor core(s) 108, node 102, and/or functionality described herein can improve the technological field of medical image analysis, medical diagnosis, and/or related treatment planning. For example, the functionality described herein can reconstruct surfaces of chunks of a colon in real-time or near real-time, which can be used for the visualization of missed colon surfaces that lead to potential missed adenomas. Further, by using recurrent neural network that predicts depth and camera poses for colonoscopic images, integrating the neural network into a SLAM system to improve tracking and eliminate drift, and fusing colonoscopic frames into a global high-quality mesh, the 3D surface of the colon can help endoscopists realize missed colon surface portions which can lead to better, more complete inspection of colon surface and potentially more removals of potentially dangerous polyps.

REFERENCES

The disclosures of all of the references listed herein are hereby incorporated herein by reference in their entireties.

[1] Engel, J., Koltun, V., Cremers, D.: Direct sparse odometry. IEEE Transactions on Pattern Analysis and Machine Intelligence (March 2018)

[2] Engel, J., Schöps, T., Cremers, D.: Lsd-slam: Large-scale direct monocular slam. In: Fleet, D., Pajdla, T., Schiele, B., Tuytelaars, T. (eds.) Computer Vision—ECCV 2014. pp. 834-849. Springer International Publishing, Cham (2014)

[3] Hong, D., Tavanapong, W., Wong, J., Oh, J., De Groen, P. C.: 3d reconstruction of virtual colon structures from colonoscopy images. Computerized Medical Imaging and Graphics 38(1), 22-33 (2014)

[4] Hong, W., Wang, J., Qiu, F., Kaufman, A., Anderson, J.: Colonoscopy simulation. In: Proc. SPIE (2007)

[5] Jemal, A., Center, M. M., DeSantis, C., Ward, E. M.: Global patterns of cancer incidence and mortality rates and trends. Cancer Epidemiology and Prevention Biomarkers 19(8), 1893-1907 (2010)

[6] Mur-Artal, R., Montiel, J. M. M., Tardós, J. D.: ORB-SLAM: A versatile and accurate monocular SLAM system. IEEE Trans. Robotics 31(5), 1147-1163 (2015)

[7] C van Rijn, J., B Reitsma, J., Stoker, J., Bossuyt, P., van Deventer, S., Dekker, E.: Polyp miss rate determined by tandem colonoscopy: A systematic review. The American journal of gastroenterology 101 (02 2006)

[8] Schönberger, J. L., Frahm, J. M.: Structure-from-motion revisited. In: Conference on Computer Vision and Pattern Recognition (CVPR) (2016)

[9] Schöps, T., Sattler, T., Pollefeys, M.: SurfelMeshing: Online surfel-based mesh reconstruction. CoRR abs/1810.00729 (2018), http://arxiv.org/abs/1810.00729

[10] Tateno, K., Tombari, F., Laina, I., Navab, N.: Cnn-slam: Real-time dense monocular slam with learned depth prediction. In: 2017 IEEE Conference on Computer Vision and Pattern Recognition (CVPR). vol. 00, pp. 6565-6574 (July 2017)

[11] Wang, R., Frahm, J., Pizer, S. M.: Recurrent neural network for learning densedepth and ego-motion from video. CoRR abs/1805.06558 (2018), http://arxiv.org/abs/1805.06558

[12] Yang, N., Wang, R., Stueckler, J., Cremers, D.: Deep virtual stereo odometry: Leveraging deep depth prediction for monocular direct sparse odometry. In: ECCV (2018)

[13] Yin, Z., Shi, J.: Geonet: Unsupervised learning of dense depth, optical flow and camera pose. In: CVPR. pp. 1983-1992 (2018)

[14] Zhou, T., Brown, M., Snavely, N., Lowe, D. G.: Unsupervised learning of depth and ego-motion from video. In: CVPR (2017)

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for deriving a three-dimensional (3D) surface from colonoscopic video, the method comprising: performing video frame preprocessing to identify a plurality of keyframes of a colonoscopic video, wherein the video frame preprocessing includes informative frame selection and keyframe selection; generating, using a recurrent neural network and direct sparse odometry, camera poses and depth maps for the keyframes, wherein generating the camera poses and the depth maps for the keyframes includes using the recurrent neural network and a number of most recent keyframes to generate frame-wise depth maps and tentative camera poses and optimizing the tentative camera poses using direct sparse odometry and wherein output generated using direct sparse odometry is used to refine the recurrent neural network for generating improved camera poses; and fusing, using SurfelMeshing and the camera poses, the depth maps into a three-dimensional (3D) surface of a colon portion, wherein the 3D surface indicates at least one region of the colon portion that was not visualized.

2. The method of claim 1 comprising:
guiding, using a display, an endoscopist back to the at least one region of the colon portion that was not visualized.

3. The method of claim 2 wherein guiding the endoscopist includes comparing, by a colon surface generation module, features in the colonoscopic video as a colonoscope heads back toward the colon portion and features identified by the colon surface generation module from the colonoscopic video and wherein guiding the endoscopist occurs in real-time or near real-time.

4. The method of claim 1 wherein the informative frame selection is performed using a convolutional neural network.

5. The method of claim 1 wherein the recurrent neural network is trained using video frames from one or more colonoscopic videos and groundtruth depth is determined using a structure-from-motion (SfM) approach to generate a sparse depth map for each of the video frames.

6. The method of claim 1 wherein the recurrent neural network is trained using a geometric consistency loss value to explicitly impose temporal consistency among depth maps generated by the recurrent neural network.

7. The method of claim 1 wherein the recurrent neural network is trained using a computed specularity mask to mask out image reprojection error at saturated regions in the video frames, wherein the computed specularity mask is determined for each of the video frames based on an intensity threshold value; and using a computed occlusion mask to mask out image reprojection error at occluded regions in the video frames, wherein the computed occlusion mask is determined by a forward-backward geometric consistency check.

8. A system for deriving a three-dimensional (3D) surface from colonoscopic video, the system comprising: at least one processor; and a colon surface generation module (CSGM) executable by the at least one processor, wherein the CSGM is configured for: performing video frame preprocessing to identify a plurality of keyframes of a colonoscopic video, wherein the video frame preprocessing includes informative frame selection and keyframe selection; generating, using a recurrent neural network and direct sparse odometry, camera poses and depth maps for the keyframes, wherein generating the camera poses and the depth maps for the keyframes includes using the recurrent neural network and a number of most recent keyframes to generate frame-wise depth maps and tentative camera poses and optimizing the tentative camera poses using direct sparse odometry and wherein output generated using direct sparse odometry is used to refine the recurrent neural network for generating improved camera poses; optimizing the tentative camera poses using direct sparse odometry; and fusing, using SurfelMeshing and the camera poses, the depth maps into a three-dimensional (3D) surface of a colon portion, wherein the 3D surface indicates at least one region of the colon portion that was not visualized.

9. The system of claim 8 wherein the CSGM is configured for:

guiding, using a display, an endoscopist back to the at least one region of the colon portion that was not visualized.

10. The system of claim 9 wherein the CSGM is configured for comparing features in the colonoscopic video as a colonoscope heads back toward the colon portion and stored features identified by the CSGM from the colonoscopic video and wherein guiding the endoscopist occurs in real-time or near real-time.

11. The system of claim 8 wherein the informative frame selection is performed using a convolutional neural network.

12. The system of claim 8 wherein the recurrent neural network is trained using video frames from one or more colonoscopic videos and groundtruth depth is determined using a structure-from-motion (SfM) approach to generate a sparse depth map for each of the video frames.

13. The system of claim 8 wherein the recurrent neural network is trained using a geometric consistency loss value to explicitly impose temporal consistency among depth maps generated by the recurrent neural network.

14. The system of claim 8 wherein the recurrent neural network is trained using a computed specularity mask to mask out image reprojection error at saturated regions in the video frames, wherein the computed specularity mask is determined for each of the video frames based on an intensity threshold value; and using a computed occlusion mask to mask out image reprojection error at occluded regions in the video frames, wherein the computed occlusion mask is determined by a forward-backward geometric consistency check.

15. A non-transitory computer readable medium having stored thereon executable instructions that when executed by a processor of a computer cause the computer to perform steps comprising: performing video frame preprocessing to identify a plurality of keyframes of a colonoscopic video, wherein the video frame preprocessing includes informative frame selection and keyframe selection; generating, using a recurrent neural network and direct sparse odometry, camera poses and depth maps for the keyframes, wherein generating the camera poses and the depth maps for the keyframes includes using the recurrent neural network and a number of most recent keyframes to generate frame-wise depth maps and tentative camera poses and optimizing the tentative camera poses using direct sparse odometry and wherein output generated using direct sparse odometry is used to refine the recurrent neural network for generating improved camera poses; and fusing, using SurfelMeshing and the camera poses, the depth maps into a three-dimensional (3D) surface of a colon portion, wherein the 3D surface indicates at least one region of the colon portion that was not visualized.

16. The non-transitory computer readable medium of claim 15 wherein the executable instructions when executed by the processor of the computer cause the computer to perform steps comprising:

guiding, using a display, an endoscopist back to the at least one region of the colon portion that was not visualized.

* * * * *